(12) United States Patent
Zony et al.

(10) Patent No.: US 11,458,068 B2
(45) Date of Patent: Oct. 4, 2022

(54) APPARATUS AND METHOD FOR PROMOTING SHALLOW BREATHING OF A PATIENT

(71) Applicant: Qfix Systems, LLC, Avondale, PA (US)

(72) Inventors: Kenne Zony, Coatesville, PA (US); Andrew Johnson, Newark, DE (US); James Manning, Newark, DE (US); Daniel D. Coppens, Avondale, PA (US)

(73) Assignee: Qfix Systems, LLC, Avondale, PA (US)

( * ) Notice: Subject to any disclaimer, the term of this patent is extended or adjusted under 35 U.S.C. 154(b) by 618 days.

(21) Appl. No.: 16/305,421

(22) PCT Filed: Jun. 2, 2017

(86) PCT No.: PCT/US2017/035743
§ 371 (c)(1),
(2) Date: Nov. 29, 2018

(87) PCT Pub. No.: WO2017/210596
PCT Pub. Date: Dec. 7, 2017

(65) Prior Publication Data
US 2021/0220217 A1    Jul. 22, 2021

Related U.S. Application Data

(60) Provisional application No. 62/345,362, filed on Jun. 3, 2016.

(51) Int. Cl.
*A61H 31/00* (2006.01)
*A61B 5/055* (2006.01)
(Continued)

(52) U.S. Cl.
CPC .......... *A61H 31/008* (2013.01); *A61B 5/055* (2013.01); *A61B 6/0414* (2013.01); *A61H 9/00* (2013.01);
(Continued)

(58) Field of Classification Search
CPC .......... A61H 31/008; A61H 2201/0103; A61H 2205/083; A61H 2230/85;
(Continued)

(56) References Cited

U.S. PATENT DOCUMENTS

| 3,454,000 A | * | 7/1969 | Bird | A61H 9/0078 601/41 |
| 3,904,195 A | * | 9/1975 | Chavanne | A61H 1/008 601/24 |

(Continued)

FOREIGN PATENT DOCUMENTS

| CA | 1225889 A | 8/1987 |
| CN | 101268940 A | 9/2008 |

(Continued)

OTHER PUBLICATIONS

International Preliminary Report on Patentability for Application No. PCT/US2017/035743, dated Dec. 4, 2018—7 pages.

(Continued)

*Primary Examiner* — Justine R Yu
*Assistant Examiner* — Alexander Morales
(74) *Attorney, Agent, or Firm* — RatnerPrestia

(57) ABSTRACT

An apparatus for promoting shallow breathing of a patient includes a paddle, a belt, and a bladder. The paddle may be configured to contact the body of the patient. The belt may be configured to secure the paddle against the body of the patient. Finally, the bladder may be interposed between the belt and the paddle in the installed condition, such that inflating the bladder urges the paddle toward the body of the patient so as to apply pressure to the abdomen of the patient. A method of promoting shallow breathing is also provided that includes attaching a paddle and a bladder to a belt, such that the bladder is between the paddle and the belt, positioning the paddle on the patient, and inflating the bladder to (Continued)

urge the paddle toward the body of the patient such that the paddle applies pressure to the abdomen of the patient.

26 Claims, 17 Drawing Sheets

(51) Int. Cl.
  *A61B 6/04* (2006.01)
  *A61H 9/00* (2006.01)
  *A61H 11/00* (2006.01)
(52) U.S. Cl.
  CPC ...... *A61H 11/00* (2013.01); *A61H 2201/0103* (2013.01); *A61H 2201/0119* (2013.01); *A61H 2201/10* (2013.01); *A61H 2201/12* (2013.01); *A61H 2201/169* (2013.01); *A61H 2201/5094* (2013.01); *A61H 2205/083* (2013.01); *A61H 2230/85* (2013.01)
(58) Field of Classification Search
  CPC ........ A61H 31/00–02; A61H 2201/149; A61H 1/006–008; A61H 11/00; A61H 2011/005; A63B 21/4039; A63B 21/4009; A63B 23/02; A63B 2071/1208; A61B 6/0421; A61B 5/7292
  USPC ......... 128/876, 830, 846, 842, 849; 607/100
  See application file for complete search history.

(56) References Cited

U.S. PATENT DOCUMENTS

| | | | | |
|---|---|---|---|---|
| 4,506,883 | A * | 3/1985 | Rathbun | A63B 23/03575 434/247 |
| 4,664,098 | A * | 5/1987 | Woudenberg | A61H 9/0078 601/106 |
| 5,251,629 | A | 10/1993 | Koizumi et al. | |
| 5,490,820 | A * | 2/1996 | Schock | A61H 9/0078 601/1 |
| 5,616,109 | A * | 4/1997 | Szu-Ming | A63B 21/4047 482/130 |
| 5,630,789 | A * | 5/1997 | Schock | A61H 31/00 601/41 |
| 5,722,987 | A * | 3/1998 | Witbeck | A61H 31/00 128/100.1 |
| 5,755,647 | A * | 5/1998 | Watnik | A63B 23/03575 482/121 |
| 5,820,535 | A * | 10/1998 | Van Der Hoeven | A63B 21/4001 482/139 |
| 5,882,284 | A * | 3/1999 | Cayne | A63B 21/4009 482/130 |
| 8,911,386 | B2 * | 12/2014 | Zacharopoulos | A61F 5/03 601/19 |
| 9,579,070 | B2 * | 2/2017 | Hamill | A61B 5/1135 |
| 2005/0080362 | A1 * | 4/2005 | Quintana | A61H 31/006 601/44 |
| 2006/0009717 | A1 * | 1/2006 | Hall | A61N 1/3968 601/41 |
| 2006/0047228 | A1 * | 3/2006 | Petelenz | A61H 31/008 601/41 |
| 2007/0191881 | A1 * | 8/2007 | Amisar | A61B 17/1325 606/203 |
| 2008/0200800 | A1 | 8/2008 | Kuhara et al. | |
| 2009/0234201 | A1 * | 9/2009 | Huang | A61B 5/4866 600/301 |
| 2012/0016179 | A1 * | 1/2012 | Paradis | A61H 31/005 600/17 |
| 2012/0101418 | A1 * | 4/2012 | Manoach | A61F 5/05825 602/13 |
| 2012/0310123 | A1 * | 12/2012 | Mossmer | A61H 31/005 601/41 |
| 2013/0041303 | A1 * | 2/2013 | Hopman | A61B 17/1325 606/203 |
| 2013/0072830 | A1 * | 3/2013 | Illindala | A61H 9/0078 601/41 |
| 2014/0024979 | A1 * | 1/2014 | Radbourne | A61H 31/006 601/43 |
| 2017/0304147 | A1 * | 10/2017 | Glenn | A61M 16/10 |

FOREIGN PATENT DOCUMENTS

| | | |
|---|---|---|
| CN | 201542220 U | 8/2010 |
| CN | 202908775 U | 5/2013 |
| CN | 203339285 U | 12/2013 |
| CN | 203451993 U | 2/2014 |
| CN | 204016291 U | 12/2014 |
| CN | 105214216 A | 1/2016 |
| CN | 105251136 A | 1/2016 |

OTHER PUBLICATIONS

International Search Report and Written Opinion for Application No. PCT/US2017/035743, dated Oct. 4, 2017—9 pages.
Ishida et al., "Impact of an Abdominal Belt on Breathing Patterns and Scan Efficiency in Whole-heart Coronary Magnetic Resonance Angiography: Comparison Between th e UK and Japan", Journal of Cardiovascular Magnetic Resonance, 2011, vol. 13. No. 71—11 pages.
Chinese Office Action for Chinese Application No. 201780046914.3, dated Dec. 28, 2021 with translation, 23 pages.
Chinese Office Action for Chinese Application No. 201780046914.3, dated Jun. 8, 2022 with translation, 20 pages.

* cited by examiner

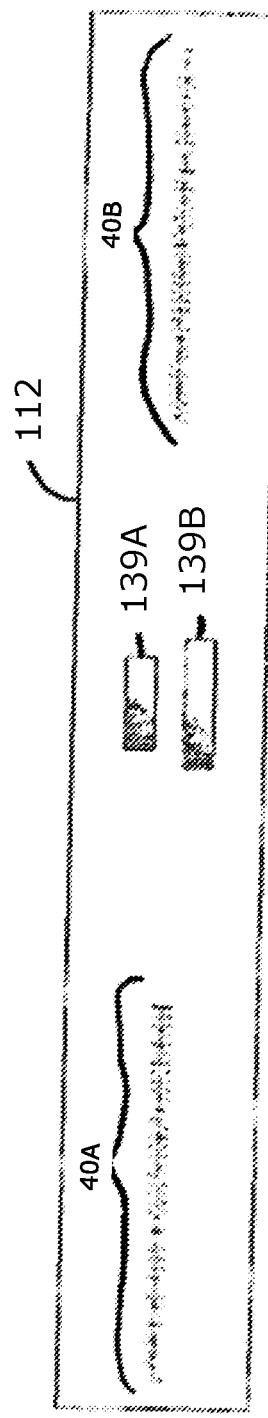
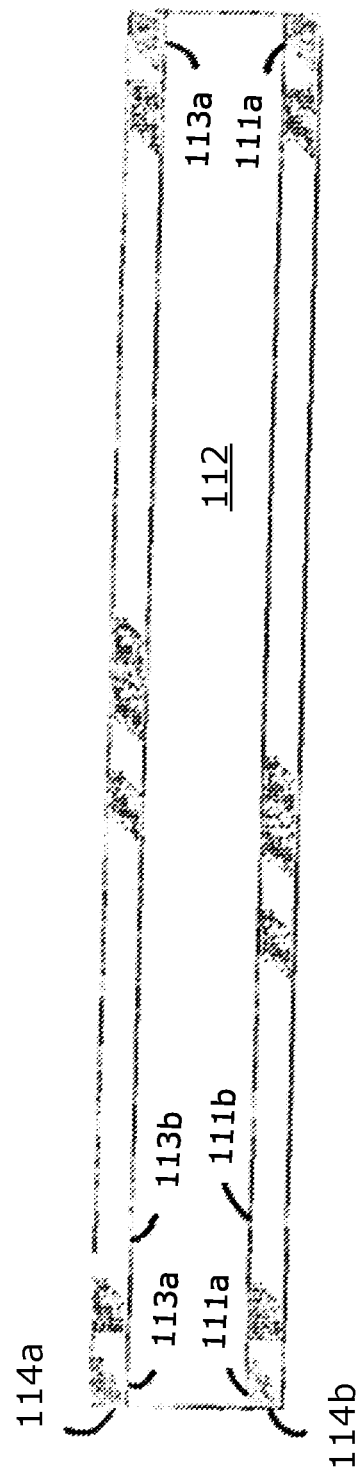

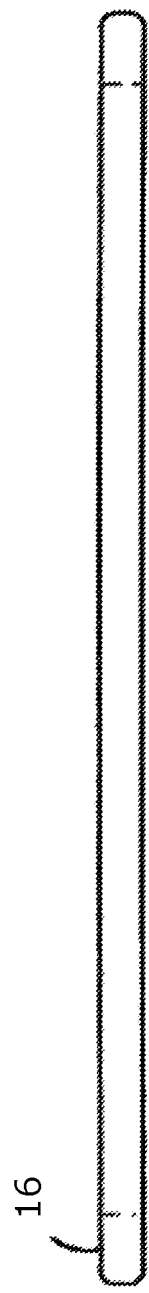
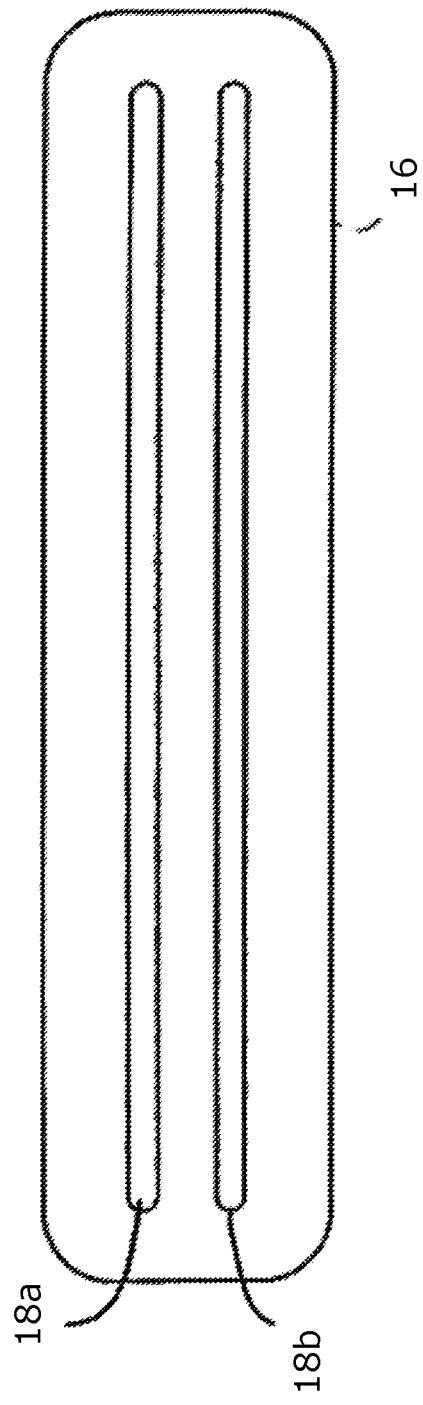
FIG. 8B
FIG. 8A

APPARATUS AND METHOD FOR PROMOTING SHALLOW BREATHING OF A PATIENT

CROSS REFERENCE TO RELATED APPLICATIONS

This application is a U.S. National Phase Application of PCT International Application PCT/US2017/035743, filed on Jun. 2, 2017, which claims the benefit of U.S. Provisional Application No. 62/345,362, entitled APPARATUS AND METHOD FOR PROMOTING SHALLOW BREATHING OF A PATIENT, filed on Jun. 3, 2016, the contents of which are incorporated herein by reference in their entirety for all purposes.

FIELD OF THE INVENTION

The present invention relates to assemblies, such as compression belts, used to promote shallow breathing of a patient.

BACKGROUND OF THE INVENTION

During radiotherapy or imaging procedures, radiation is directed towards a specific area of the patient's body to obtain a scan or to treat tumors, for example. Scanning or imaging may or may not involve radiation and includes modalities such as X-ray, CT, MRI, and PET. Often the initial scan is relied upon to identify the location of the tumor, which is subsequently treated with radiation. Thus, for scanning and treatment procedures that are performed sequentially and repeatedly, it is especially critical that the position of the patient's body is maintained relatively still to determine an accurate location of the tumor or other anatomical feature during scanning and that the position of the patient is maintained relatively consistent between each scan and treatment, so that most of the radiation is focused on the expected location of the tumor rather than healthy tissue. It is also important to limit patient motion during inter-operative procedures requiring accuracy, such as needle biopsies.

To ensure that a patient remains relatively still during the medical procedure, many devices have been employed that promote shallow breathing of the patient. However, several disadvantages are associated with the mechanisms employed to promote shallow breathing. There is therefore a need to provide an improved apparatus and method for promoting shallow breathing of a patient during imaging, radiotherapy, and other procedures.

SUMMARY OF THE INVENTION

It is a first aspect of the present invention to provide an apparatus for promoting shallow breathing of a patient. The apparatus may comprise a paddle, a belt, and a bladder. The paddle may be configured to contact the body of the patient. The belt may be configured to secure the paddle against the body of the patient. Finally, the bladder may be interposed between the belt and the paddle in the installed condition, such that inflating the bladder urges the paddle toward the body of the patient so as to apply pressure to the abdomen of the patient.

It is another aspect of the present invention to provide a method of promoting shallow breathing of a patient. The method comprises the steps of attaching a paddle and a bladder to a belt, such that the bladder is between the paddle and the belt, positioning the paddle on the patient, and inflating the bladder to urge the paddle toward the body of the patient such that the paddle applies pressure to the abdomen of the patient.

BRIEF DESCRIPTION OF THE DRAWINGS

The invention is best understood from the following detailed description when read in connection with the accompanying drawings, with like elements having the same reference numerals. When a plurality of similar elements are present, a single reference numeral may be assigned to the plurality of similar elements with a small letter designation referring to specific elements. When referring to the elements collectively or to a non-specific one or more of the elements, the small letter designation may be dropped. This emphasizes that according to common practice, the various features of the drawings are not drawn to scale unless otherwise indicated. On the contrary, the dimensions of the various features may be expanded or reduced for clarity. Included in the drawings are the following figures:

FIG. 7A is a plan view of a belt according to a second embodiment of the present invention;

FIG. 7B is a plan view of the opposite side of the belt of FIG. 7A;

FIG. 8A is a top plan view of a belt loop of the first embodiment of FIG. 1A;

FIG. 8B is a side view of the belt loop of the first embodiment of FIG. 1A;

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention. In addition, the invention may be described herein with reference primarily to application in radiation therapy, including simulation by various modalities such as CT and MRI. However, the invention is suitable for any procedure in which shallow breathing is desirable.

Referring generally to an embodiment of the invention illustrated in the figures, an apparatus 10 is provided for promoting shallow breathing of a patient. The apparatus 10 includes a paddle 24 configured to contact the body of the patient. The apparatus 10 also includes a belt 12 configured to secure the paddle 24 against the body of the patient. A bladder 22 is interposed between the belt 12 and the paddle 24 in the installed condition. The bladder 22 is inflatable to urge the paddle 24 toward the body of the patient so as to apply pressure to the abdomen of the patient.

Figure 1B:
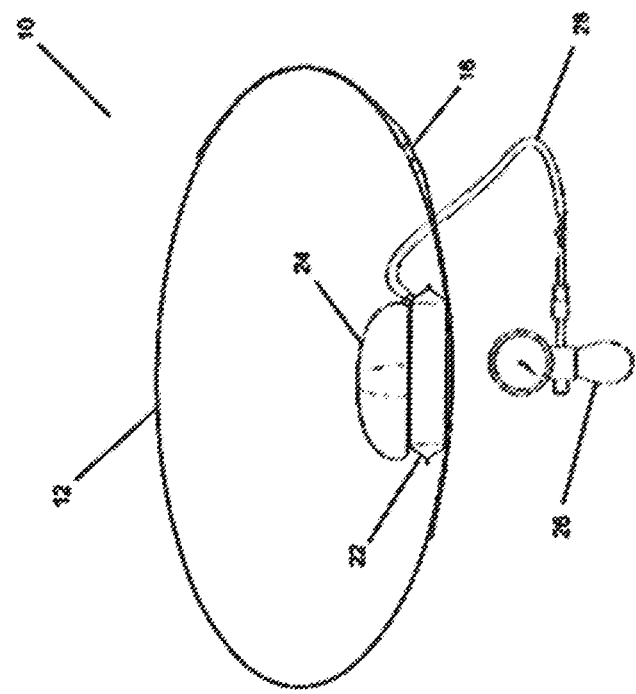
FIG. 1B is a top plan view of the compression belt of FIG. 1A attached to the hand pump.
Figure 1A:
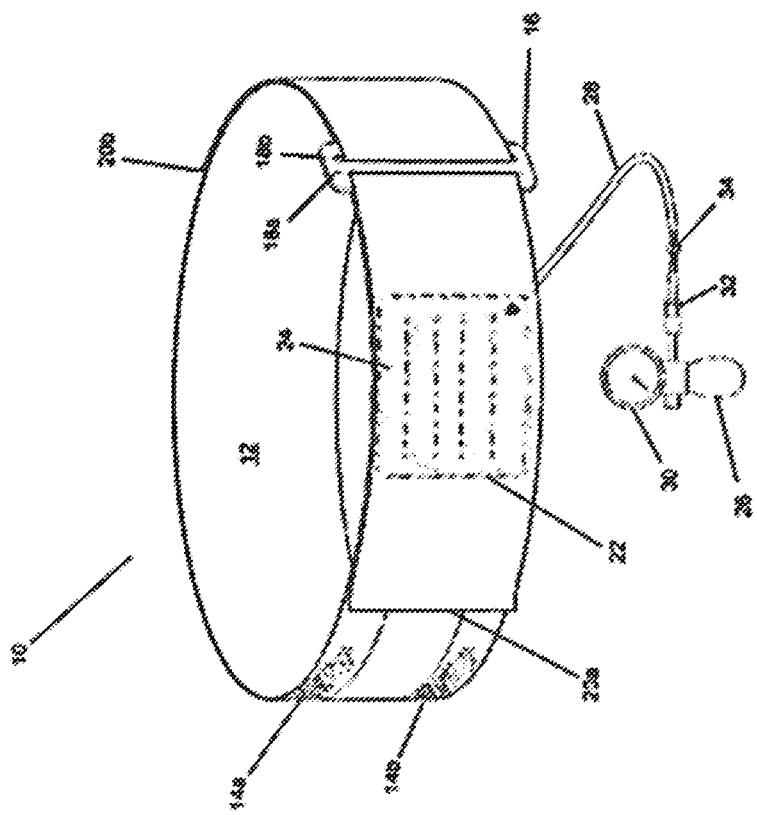
FIG. 1A is a top perspective view of a compression belt attached to a hand pump according to a first embodiment of the present invention.

Referring now to the figures in greater detail, wherein like numerals refer to the same or similar elements, an apparatus 10 according to a first embodiment of the present invention is illustrated in FIGS. 1A and 1B. The apparatus 10 comprises a belt 12, a bladder 22, and a paddle 24.

The belt 12 may comprise a layer of material having fasteners 14a, 14b applied to one side. In the embodiment illustrated in FIG. 1A, the fasteners 14a, 14b are in the form of two substantially parallel strips of hook and loop fasteners adhered along the long edges of the sheet material of the belt 12. The opposite ends 20a, 20b of the belt 12 are inserted through a respective slot 18a, 18b of a belt loop, such that the end regions of the belt 12 may be folded onto itself and allow contact of the hook and loop fasteners 14a, 14b. For example, as shown in the embodiment of the belt 112 in FIG. 7B, each strip 114a, 114b of fasteners may include a hook section 113a, 111a that is folded onto a loop section 113b, 111b. Although the embodiment disclosed in FIG. 1A may be formed of a single layer of material having two end portions that are coupled to each other, other embodiments (e.g., those disclosed below) may include a belt configured to couple to an object other than itself (e.g., a patient surface, a gurney, etc.). For example, the belt may comprise of at least one strap that couples bladder 22 and paddle 24 to a patient surface, such that pressure may be applied to the abdomen of the patient.

The length of the perimeter of the belt 12 may be adjustable by reducing or increasing the amount of material of the belt 12, which is folded onto itself. Other fasteners and mechanisms known by those of skill in art may also be incorporated, such that the length of the perimeter of the belt may be adjustable. For example, other fasteners and mechanisms that may be used include, but are not limited to, ratchet systems, plastic snap buttons, hook and grommet couplings, zippers, clasps, clamps and clamp buckles.

As would be appreciated by those of skill in the art, increasing the width of the belt distributes the cinching force of the belt across a wider area along the patient's torso. A narrow belt may concentrate the force and cause folding of the patient's skin. This may contribute to discomfort, as well as introduce error into the ability of the user to position the apparatus in the same location on the patient over the course of multiple imaging and/or radiotherapy treatment sessions.

If the apparatus is intended for use in radiotherapy or imaging applications, it is preferred that the belt be made of radiolucent materials. It is also preferred that the belt be constructed so as to minimize folding and prevent disruption or cause uneven radiation through the material. To minimize the thickness of the belt and facilitate an easier and more cost-effective method of manufacture, it is preferred that the belt is made from a weldable material to avoid the need for additional fastening material, such as adhesives or sewing. Examples of belt materials include, but are not limited to, nylon, PEEK composites, urethane backed nylon, PVC, and polyester.

Referring again to FIGS. 1A and 1B, a paddle 24 is provided and a bladder 22 is attached between an inner surface of the belt 12 and a substantially flat surface of the paddle 24. A hand pump 26 provided with a pressure gauge 30, such as a sphygmomanometer pump, is fluidly connected via a hose 28 to the bladder 22.

As would be understood by those of skill in the art, other means may be utilized to inflate the bladder, such as a pressurized air source that is commonly found in hospital rooms. A manually operated pneumatic pump may be used to control the pressure within the bladder. Alternatively, an automated system configured to vary the pressure over time such that periods of high pressure are used to severely limit motion. The automated system may also reduce pressure to allow the patient to breathe easily during certain periods of the medical procedure when shallow breathing is less critical. For example, if the apparatus is used in an radiotherapy or imaging application, the pressure control program may be linked to the function of the scanner or linear accelerator to increase the pressure during periods when shallow breathing is especially critical.

A quick-disconnect coupling 32 may be provided to disconnect the hand pump 26 from the hose 28, as well as a means for maintaining or releasing the pressure within an inflated bladder 22 after the pump 26 has been removed. The means for maintaining or releasing pressure may include a mechanical or electro-mechanical device—positioned to partially resist or completely prevent flow of inflation fluid from the bladder—including, but not limited to, one or more of a hemostat, a clamp, a valve, a regulator, a cap, or any other device known to a person having skill in the art for maintaining or releasing pressure. The means for maintaining or releasing pressure may be positioned, e.g., at or near an inlet or opening to the bladder; within or external to the bladder; or remotely from the bladder. In the embodiment illustrated in FIGS. 1A and 1B, for example, the means for maintaining or releasing pressure includes a valve 34.

In some embodiments, the coupling 32 and valve 34 may be provided as a single piece. The coupling 32 enables the hand pump 26 to be removed, such that the remainder of the apparatus 10 may be used in an MRI environment because the remaining features of the apparatus 10 may be made of MR-safe materials or less preferably, MR-conditional materials. As used herein in the specification and the claims, "MR-safe" means that the device poses no known hazards in all MRI environments as defined in ASTMF2503-13. The term "MR-conditional" is used herein in the specification and claims as defined in ASTM F2503-13 as well.

Figure 2:
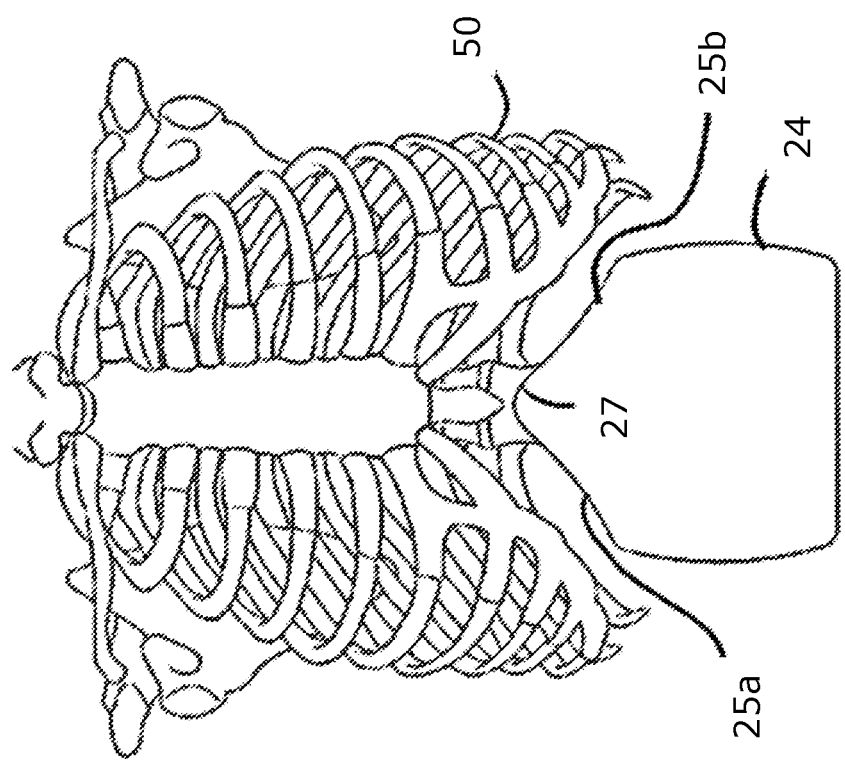
FIG. 2 is a top plan view of a paddle of the first embodiment of FIG. 1A positioned relative to a skeletal torso.
Figure 3A:
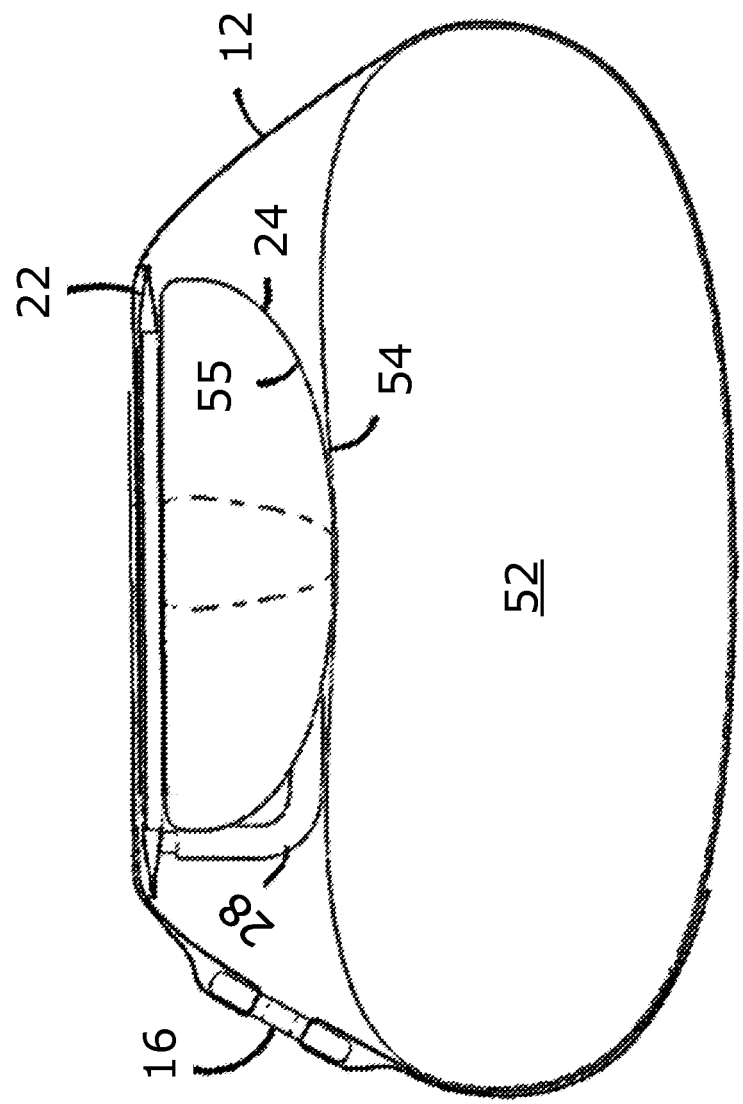
FIG. 3A is a front cross-sectional view of the first embodiment of FIG. 1A in an installed deflated condition.
Figure 3B:
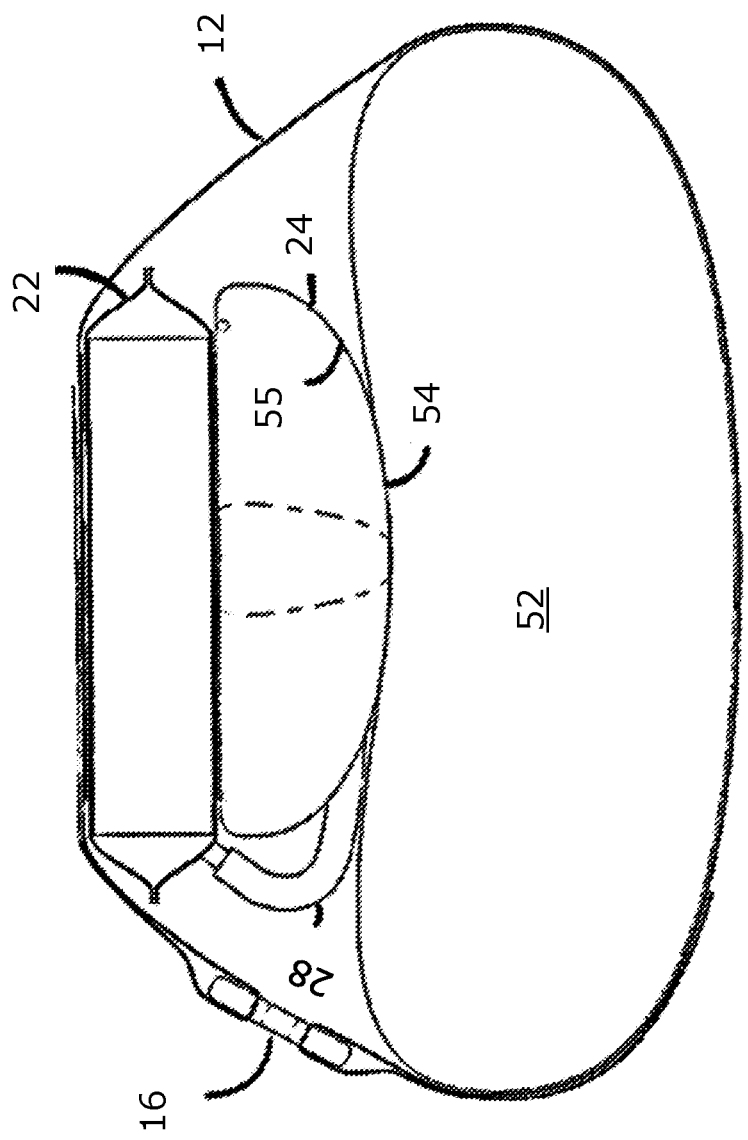
FIG. 3B is a front cross-sectional view of the first embodiment of FIG. 1A in an installed inflated condition.

The paddle incorporated in the various embodiments of the present invention may be positioned on a patient's abdomen and is preferably configured to fit inferior to a patient's Xiphoid process and between the costal cartilage, more preferably over the epigastric region of the patient's abdomen. For example, referring to FIG. 2, the paddle 24 includes two sloped sides 25a, 25b that meet to form a tip region 27A, such that paddle 24 may be nestled between and adjacent to the ribs 50 of the patient. Tip region 27A may have a length L2 that is 10-50% of the length L1 of paddle 24 as measured at the section of tip region 27A having the largest length L2. For example, length L2 of tip region 27A may be 15-45%, preferably 20-40%, more preferably 25-35%, or more preferably 27-32% of length L1 of paddle 24, as measured at the section of tip region 27A having the largest length L2.

Tip region 27A may have a depth D2 that differs from a depth D1 of a center region 27B of paddle 24. For example, depth D2 of tip region 27A may be less than depth D1 of center region 27B of paddle 24, such that compression of the patient's abdomen applies pressure to patient's internal organs and/or tissues directed toward the diaphragm. Alternatively, depth D2 of tip region 27A may be greater than depth D1 of center region 27B of paddle 24, such that urging paddle 24 toward the patient applies more compression at the region of tip region 27A of paddle 24 than at a center region 27B of paddle 24.

The patient-facing surface of the paddle can be provided with a wide variety of shapes and sizes and contours. According to one embodiment of the invention, for example, the patient-facing surface of the paddle is non-planar, such as by including a convex contour, so that appropriate pressure can be applied to the appropriate patient anatomy. Examples of non-planar surfaces are illustrated in FIGS. 1B, 3A, 3B, 4C, 9, 11, 13, and 14.

By providing such a non-planar patient-facing surface, the pressure applied to the patient at the perimeter edges of the paddle is less concentrated; instead, the point of maximum pressure can be focused toward a location that is spaced from the perimeter edges of the paddle and moved to a location corresponding to the patient's target anatomy of interest (e.g., the patient's diaphragm). Accordingly, the paddle can be contoured for various uses and applications.

The sloped sides 25 may be configured to be concave to nest within the sub-xiphoid area of the patient. Although the concavity of sloped sides 25, if present, is preferably minimal, the concavity of sloped sides 25 improves the positioning of paddle 24 nestled between and adjacent to the ribs 50 of the patient. In one embodiment, sloped sides 25 have a concavity that corresponds to the average convexity of an adult's ribcage.

The sloped sides 25 may include a portion having a curvature corresponding to an arc having a radius R1. Although the curvature of sloped sides 25 may correspond exactly to a segment of a circle having a radius R1, sloped sides may correspond to a segment of a circle within some deviation from a circular arc, such as within a 10% deviation or more. Also, the radius R1 of one or both of the curvatures of sloped sides 25 can be large or even approach infinity, thereby providing sloped sides 25 with a straight or substantially straight edge.

Tip region 27A may also have an edge 27C corresponding to a segment of an arc having a radius R2. In one embodiment, radius R1 associated with sloped sides 25 is greater than radius R2 associated with edge 27C of tip region 27A, such that the curvature of sloped sides 25 is more gradual than the curvature of edge 27C of tip region 27A. For example, radius R1 may be greater than radius R2 by 50% or more, 100% or more, 150% or more, 200% or more, 250% or more, 300% or more, 350% or more, 400% or more, 500% or more, 600% or more, or 700% or more.

By configuring paddle 24 such that the curvature of sloped sides 25 (25a and/or 25b) is more gradual than the curvature of edge 27C of tip region 27A, paddle 24 may be configured to have a contour that advantageously conforms to the anatomy of the patient. This, in turn, applies pressure on the requisite area within the lower half of the patient's torso for promoting shallow breathing. More specifically, such a contour allows the paddle to become nestled adjacent the patient's Xiphoid process and between the costal cartilage. Additionally, such a contour facilitates intuitive orientation, alignment, and placement of the paddle for optimal promotion of shallow breathing.

By providing the paddle with a tip such as tip region 27a according to some embodiments of the invention, the paddle becomes asymmetrical to facilitate the positioning of the paddle adjacent to the patient's relevant or target anatomy. Such asymmetry also provides confirmation of the correct orientation of the paddle, such as by orienting the paddle so that a region of the paddle, such as tip region 27a, faces in a direct toward the patient's Xiphoid process.

It is preferred that the configuration of the paddle is such that the paddle will generally occupy most of the open area and comfortably nest between the patient's ribs close to the sternum rather than press against the ribs. It is preferred to provide the paddle with this shape to facilitate repeated positioning of the paddle in the same location over the course of several imaging and/or radiotherapy sessions. Additionally, the shape of the paddle may concentrate compression on the requisite area within the lower half of the torso for inducing compression-based shallow breathing. While other shapes, such as a rectangle, may be utilized in this invention, preferred embodiments of the invention may have alternative shapes configured to reduce any concern that the application of pressure will be impeded by the ribs, thereby using such alternative shapes for improving the effectiveness of the compression on the abdomen or requiring less pressure to compensate and avoiding needless discomfort to the patient.

It has been discovered that embodiments of a paddle according to aspects of this invention can avoid compression of lower ribs and/or avoid a lack of consistent pressure. For these reasons, paddles according to preferred aspects of this invention are more effective for promoting shallow breathing of a patient.

Although various embodiments and configurations of a paddle have been described, including various possible contours and shapes and dimensional features and proportions, it will be appreciated that the paddle can be provided with a wide variety of configurations, contours, shapes, dimensional features, and proportions without departing from the spirit or scope of this invention.

Paddle 24 includes at least one rigid section, which may be in the form of a layer of material. Preferably, the rigid section does not significantly deform such that paddle 24 provides a consistent and/or uniform force to promote shallow breathing. In one embodiment, the rigid section advantageously enables paddle 24 to apply amounts of pressure corresponding to the contoured shape of paddle 24 to the patient. The rigid section of paddle 24 may be a section of the core of paddle 24. An outer layer formed of a soft material may be interposed between the rigid section of paddle 24 and the patient to promote comfort of the patient. The rigid section may be formed of a material that provides sufficient rigidity, such as, e.g., open cell foam materials, closed cell foam materials, plastics, metals, ceramics, composites, etc. As mentioned above, however, paddle 24 is preferably MR-safe or MR-conditional.

Although paddle 24 may be configured to have a rigid section as noted above, paddle 24 may alternatively have a hollow or partially hollow interior region. Such a region may be rigid so as not to permit collapse or significant deformation of the paddle 24. Alternatively, the paddle 24 may be inflatable to become relatively rigid. In a preferred embodiment, when used in conjunction with a bladder, such an inflatable paddle is inflatable to a higher pressure than that of the bladder. It may, however, be inflatable to a pressure equal to or even less than the bladder so long as it can help promote shallow breathing.

In the case of an inflatable paddle, and when used in conjunction with a bladder, the paddle can be a separate component from the bladder or can alternatively be formed integrally with the bladder. For example, the bladder and paddle can be sections of a single component, separated by a wall, thereby defining separate compartments inflatable to different or even the same pressures, as needed. In such an embodiment, the bladder and paddle can be inflated using the same inflation device, and can utilize the same or different means for maintaining or releasing pressure.

Figure 6:
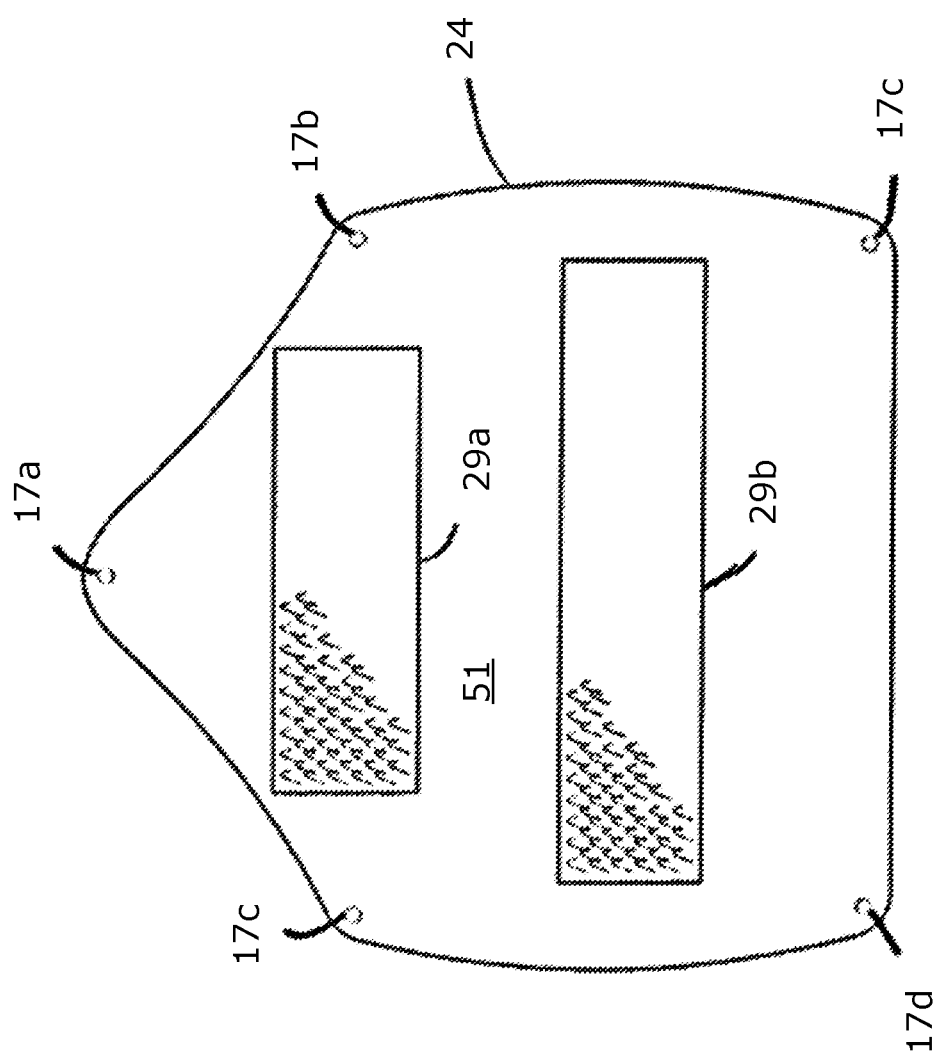
FIG. 6 is a bottom plan view of the paddle of the first embodiment of FIG. 1A.

In some embodiments of the present invention, a plurality of fiducial markers may also be embedded in the paddle. Fiducial markers are designed to be tracked through modalities such as x-ray, MRI, RF tracking, etc. They may provide a surrogate location for the paddle and point of reference for a tumor, for example. The markers are generally tracked back to their position at the time of simulation for treatment. These fiducial markers include, but are not limited to, gold seed markers, Calypso® beacons, other x-ray markers, MRI markers, etc. as known to one skilled in the art. The markers may be embedded in the paddle to enable the identification of the location as well as orientation of the apparatus. The use of at least three markers may also enable three-dimensional triangulation of the position of the paddle and or tumor. For example, referring to FIG. 6, a plurality of x-ray opaque markers 17a-17e may be associated with a paddle 24 to allow interpolation of the location of a tumor. These markers may also be attached or embedded in other parts of the apparatus made according to the present invention.

In order to induce or promote shallow breathing, a constant pressure is applied by the paddle to the patient's abdomen to minimize the expansion and contraction of the lower half of the torso during inhalation and exhalation. This pressure is applied by a combination of belt tightening and bladder inflation. For example, referring to FIGS. 3A and 3B, a torso 52 is schematically represented with an apparatus according to the present invention in the installed condition. The belt 12 has been cinched through the belt loop 16, such that the paddle 24 is compressed against the patient along abdominal surface 54. As air is delivered to bladder 22 through hose 28, the bladder 22 increases the pressure exerted upon abdominal surface 54 by the paddle 24. The top surface 55 of the paddle 24 is preferably contoured to reduce patient discomfort as the pressure against the abdominal surface 54 increases.

As previously noted, it is an aspect of the present invention to provide an apparatus that will allow the user to repeatedly position the apparatus in the same location relative to the patient over a series of imaging and radiotherapy sessions. When the bladder is deflated, this may be a relatively simple task. For example, referring to FIG. 7A, the belt 112 may be provided with graduated markings 40a, 40b that may be recorded by the user to ensure that the belt 112 is cinched to the same position during each imaging and radiotherapy session. The markings may be read at the belt loop, such as belt loop 16, where the belt is folded onto itself. When the bladder is inflated, the paddle may tend to shift or rock.

To better control the positioning of the paddle 24 as the bladder 22 is inflated, the apparatus 10 according to the various embodiments of the present invention may include several features. For example, by incorporating a pressure gauge 30, the user may pressurize the bladder 22 to substantially the same degree during each imaging or therapy session to ensure that the same or similar amount of force is applied by the paddle to the patient's abdomen 52. Also, to ensure that the force resulting from the expansion of the bladder 22 is applied evenly to paddle 24, the paddle 24 may be provided with a relatively flat surface and the bladder 22 may be configured to control the geometry of the bladder 22 upon inflation.

For example, referring to the embodiment illustrated in FIGS. 4A to 4E, a paddle 24 having a relatively flat surface 51 in contact with one side of a bladder 22 is illustrated. The bladder 22 is expanded by delivering a fluid, such as air, to the inner volume of the bladder 22 through a port 23 attached and extending from an outer surface of the bladder 22. As would be appreciated by those of skill in the art, the port 23 for delivering fluid to the bladder 22 may be located on any point on the surface of the bladder 22. Alternatively, in other embodiments, the port may be incorporated in or through the paddle, as long as an additional fluid connection point is provided between the paddle and the bladder.

Figure 4A:
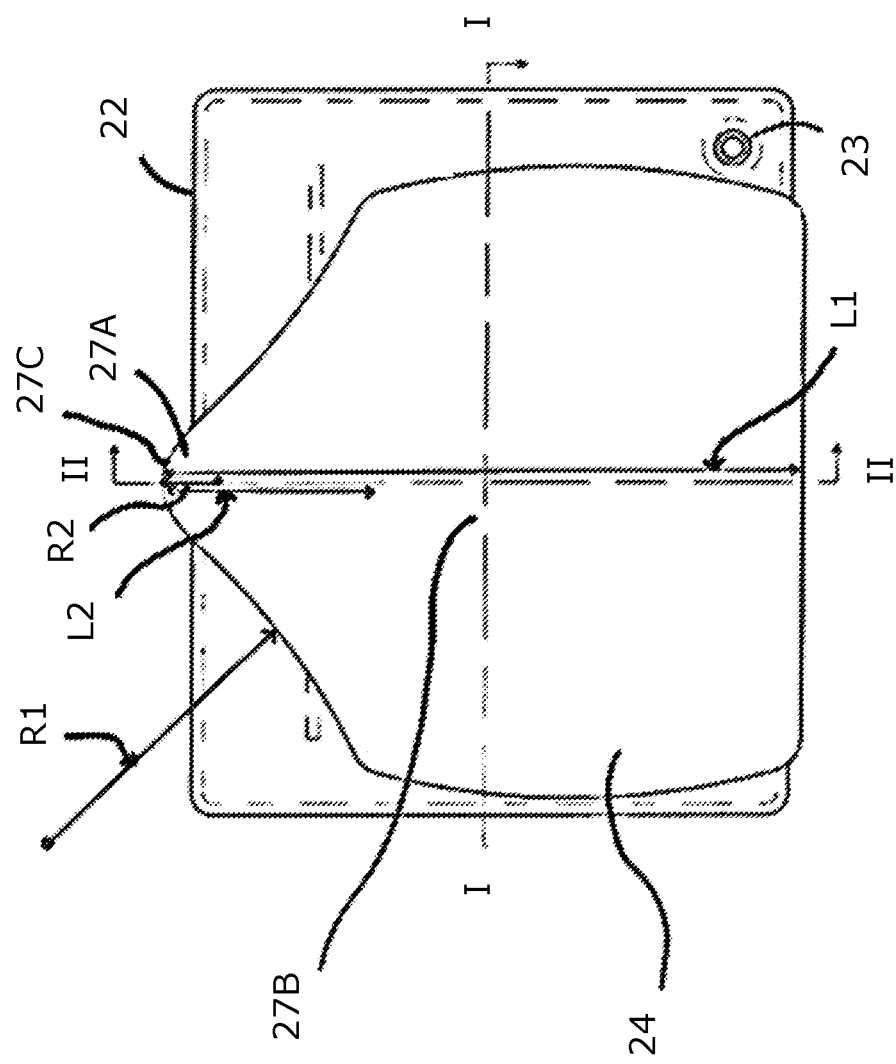
FIG. 4A is a top plan view of a paddle and bladder of the first embodiment of FIG. 1A.
Figure 4C:
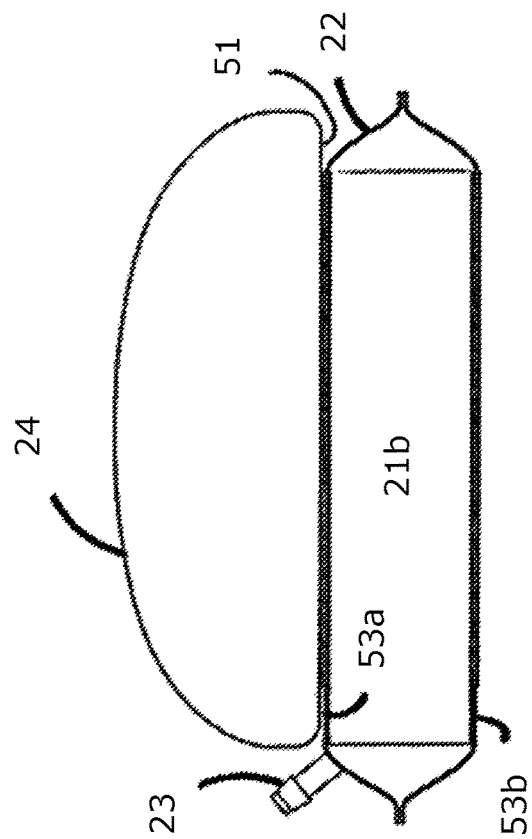
FIG. 4C is a cross-sectional rear view of the paddle and bladder of FIG. 4A in an inflated condition along axis I-I.
Figure 4B:
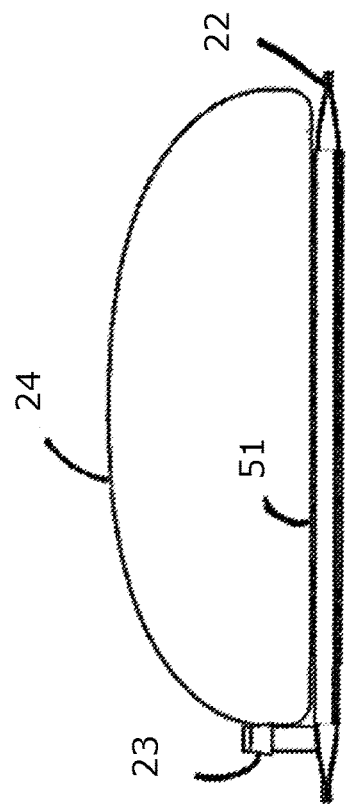
FIG. 4B is a cross-sectional rear view of the paddle and bladder of FIG. 4A in a deflated condition along axis I-I.
Figure 4E:
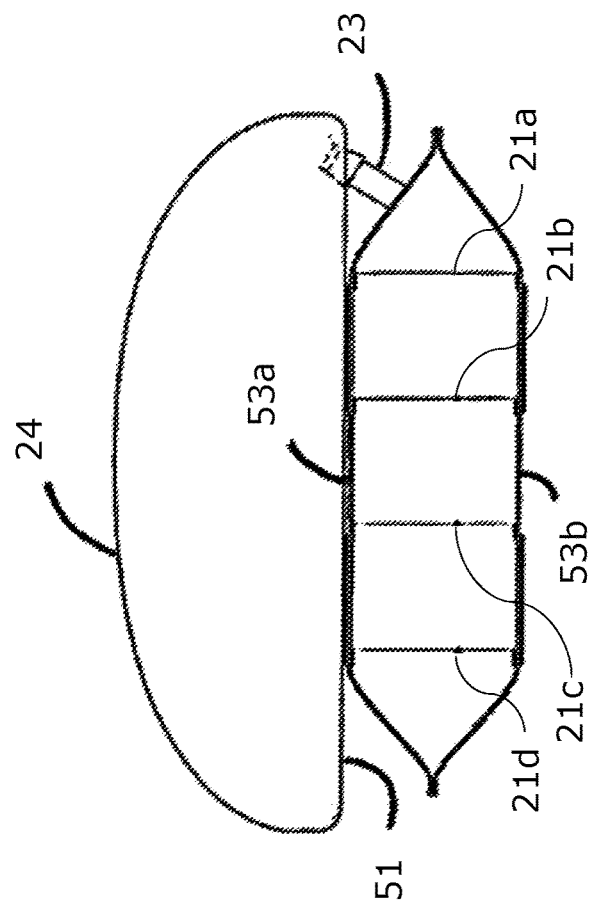
FIG. 4E is a cross-sectional side view of the paddle and bladder of FIG. 4A in an inflated condition along axis II-II.
Figure 4D:
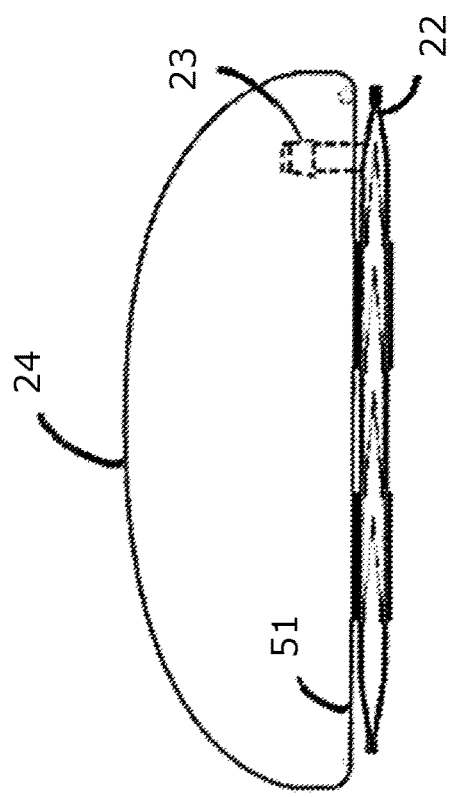
FIG. 4D is a cross-sectional side view of the paddle and bladder of FIG. 4A in a deflated condition along axis II-II.
Figure 5:
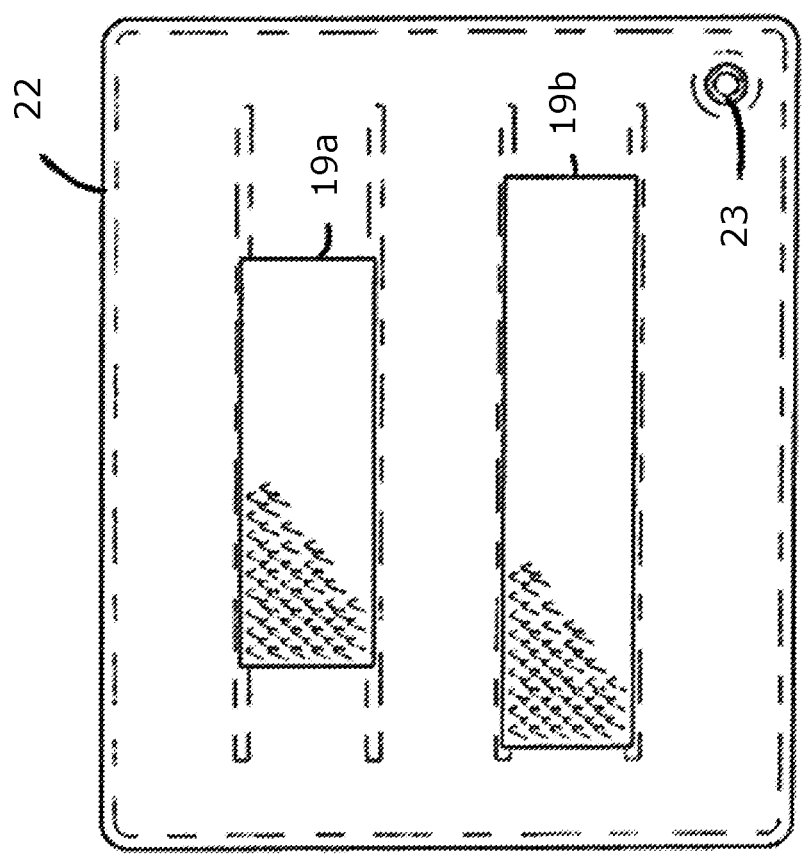
FIG. 5 is a top plan view of the bladder of the first embodiment of FIG. 1A.

As best shown in FIGS. 4C, 4D, and 4E, the bladder 22 may be provided with a plurality of baffles 21a-d to control the shape of the bladder 22 as it expands. The height and length of the baffles 21a-d are substantially equal and the spacing between baffles is preferably even, so that ballooning of the bladder is prevented. A rounded surface will reduce the contact between the bladder and the paddle, i.e. the bladder will separate from the paddle, thereby increasing the risk of rocking or shifting of the paddle out of its desired position on the patient's abdomen. The same is true of the contact between the bladder and the belt. Ballooning of the bladder may cause the belt to shift and increase the likelihood that the paddle will shift during inflation. Therefore, the baffles 21a-d are preferably configured to provide a two substantially parallel, flat surfaces 53a, 53b when the bladder 22 is inflated to maximize contact between the paddle 24, bladder 22, and belt. In addition to the use of baffles, the configuration of the inflated bladder may be controlled based on the location and dimensions of the welds around the perimeter of the bladder.

In the embodiment illustrated in FIGS. 4A to 6, the bladder 22 and paddle 24 are two separable elements. The bladder 22 and paddle 24 may be removably attached to each other using one or more fasteners, such as one or more strips of hook and loop fasteners 19a, 19b, 29a, 29b applied to the opposing surfaces of the bladder 22 and paddle 24.

In another embodiment of the present invention, the bladder 22 may not be removable from the flat surface 51 of the paddle 24. For example, the bladder may comprise an expandable sheet material that is bonded to the flat surface of the paddle, such that the flat surface of the paddle forms a portion of the boundary of the enclosed inner volume of the bladder. In this embodiment, the internal baffles used to control the shape of the bladder as it is inflated may be bonded to the paddle and the expandable sheet material of the bladder.

In order to attach the bladder to the belt, the same or different fasteners may be applied on both sides of the bladder. For example, strips of hook and loop fasteners may be applied to opposite sides of the bladder with corresponding strips located on the flat surface 51 of the bladder 22 and on one side of the belt, such as the strips 139a, 139b illustrated in FIG. 7A.

The present invention further includes a method of promoting shallow breathing of a patient by using an apparatus as described above. Referring again to FIGS. 3A and 3B, the steps of the method may include first attaching a paddle 24 and a bladder 22 to a belt, such that the bladder 22 is between the paddle 24 and the belt 12. The surface of the paddle 24 in contact with the bladder 22 is preferably a substantially flat surface. The user may then position the paddle 24 on the patient 52 on the patient's abdominal area 54 and between the patient's ribs. The surface 55 of the paddle 24 in contact with the patient's abdominal area 54 is preferably a contoured surface. The method also includes cinching the belt 12 to a desired loop length and inflating the bladder 22 to urge the paddle 24 toward the body of the patient such that the paddle applies pressure to the abdominal area 54 of the patient 52. The user may inflate the bladder with a hand pump associated with a pressure gauge to inflate the bladder to a desired pressure level. As best viewed in FIGS. 3A and 3B, it is preferred that the bladder 22 is configured, such that when the bladder 22 is inflated, the distance between the paddle 24 and the belt 12 is substantially equal across the flat surface 51 of the paddle 24.

It is possible, according to the apparatus and method of this invention, to provide an improved method of promoting shallow breathing of patients during imaging or therapeutic treatment. For example, it has been discovered that the paddle may be more easily relocated between imaging and therapy sessions and compressed against the patient by interposing the bladder between the belt and the paddle. Although the bladder may alternatively be positioned between the paddle and the patient, it has been discovered that interposing the bladder between the belt and the paddle, rather than the common practice of placing the bladder between the paddle and the patient, provides an improved apparatus that allows for the repeated positioning of the paddle in the same or similar location.

By positioning a bladder between a paddle and the belt, the paddle may be provided in the form a solid contoured piece. As mentioned above, the paddle is preferably formed of at least one rigid section such that a consistent and uniform force is applied to the patient. Therefore, the shape of the contoured surface against the patient's abdomen is not subject to change, unlike a bladder whose shape may be influenced by various forces, such as the patient's breathing, mechanical force from the belt, and repeated inflation and deflation between and during therapy and imaging sessions. Furthermore, by controlling the configuration of the bladder during inflation so that the area of compression by the paddle is even and repeatable, rocking or shifting of the compression surface against the patient's abdomen is reduced and/or prevented.

FIGS. 9-13 depict four additional embodiments of the invention. Apparatuses 100, 200, 300, and 400 are similar to apparatus 10, but include at least the differences disclosed herein. Accordingly, where the apparatuses 10, 100, 200, 300, and 400 utilize similar features, the same reference numbers are applied.

Figure 9:
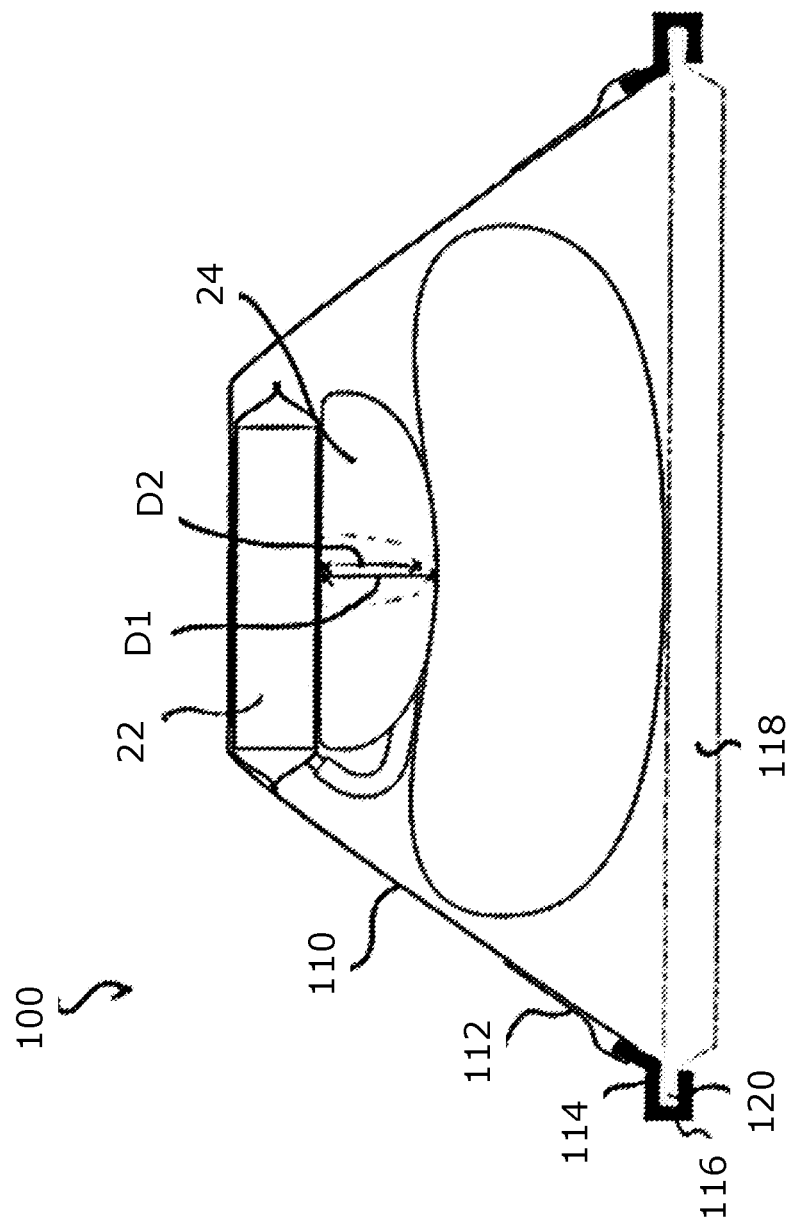
FIG. 9 is a side view of an apparatus for promoting shallow breathing of a patient according to a third embodiment of the present invention.
Figure 10:
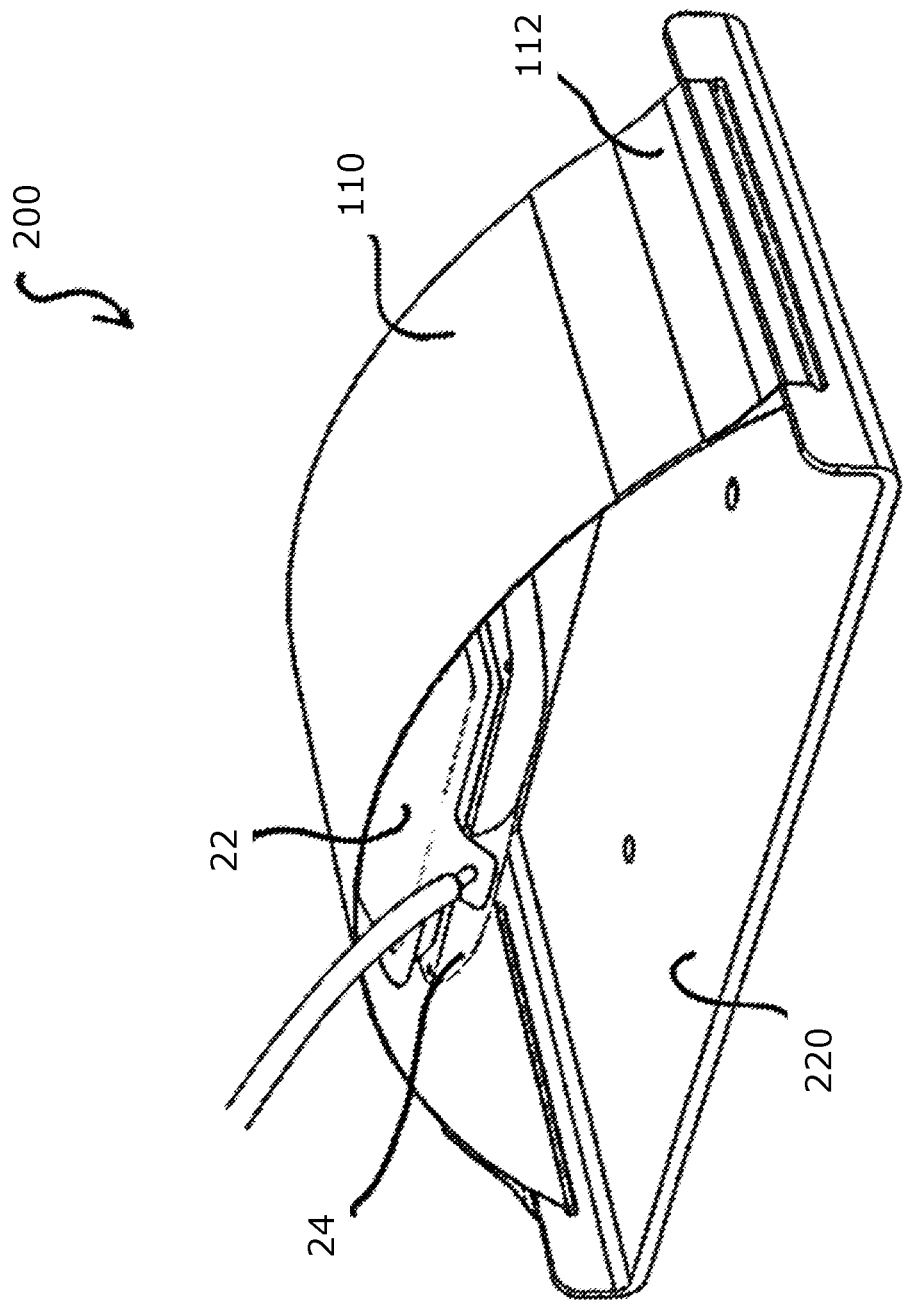
FIG. 10 is a perspective view of an apparatus for promoting shallow breathing of a patient according to a fourth embodiment of the present invention.

As a general overview, apparatus 100 includes paddle 24, bladder 22, and belt 110. Belt 110 is configured to be coupled to a patient surface 118, such as a patient's bed, a patient couch top, a gurney, a counter top, an immobilization device, a device for use in stereotactic body radiation surgery (SBRT), a lung treatment device, a chair, an imaging or treatment modality, or any other surface that supports a patient. Belt 110 may be attached to at least one coupler 114 at one or more end regions 112 of belt 110. For example, belt 110 may extend through a loop in coupler 114 and fold onto itself, e.g., to allow contact of a hook and loop fastener 14a, 14b. Although belt 110 is illustrated as a single continuous item, in one embodiment, the belt may be formed of two or more straps that maybe attached to flat surfaces 53a and/or 53b of bladder 22. Coupler 114 may have a coupler termination 116 in the form of a hook, clamp and clamp buckle, latch, threaded engagement, quarter-turn tread engagement, quick-release fasteners, ratchet mechanism, snap connector, zipper, hook and grommet coupling, clasp, or any other means of attachment known to one skilled in the art. As illustrated in FIG. 9, the coupler termination 116 may be configured to connect to an edge 120 of patient surface 118.

Apparatus 100 is configured to apply pressure to the abdomen of the patient by inflating bladder 22 and/or tightening belt 110 to urge paddle 24 toward the patient. Advantageously, the force applied by apparatus 100 is in the direction of the urging of paddle 24. For example, a significant portion, e.g., at least 70%, preferably at least 80%, preferably at least 90%, preferably at least 95%, preferably at least 97% of the force applied by apparatus 100 is in the direction of the urging of the paddle or in the normal force applied by patient surface 118. In one embodiment, all of the force applied by apparatus 100 to the patient is in the direction of the urging of paddle 24 or the opposed normal force of the patient surface. In another embodiment, belt 110 does not contact the patient, such that apparatus 100 does not apply a force to the patient directly from belt 110.

As a general overview, apparatus 200 includes paddle 24, belt 110, bladder 22, and surface 220. During use, paddle 24 is preferably positioned on one side of the patient, while surface 220 is positioned on an opposite side of the patient. Surface 220 and belt 110 are configured to apply pressure and together compress a patient's abdomen therebetween. In one embodiment, surface 220 is rigid, such that belt 110 may be accurately tightened and/or bladder 22 inflated without surface 220 bending significantly under the patient's weight, the tightness of the belt and/or inflation of bladder 22.

Similar to apparatus 100, apparatus 200 is configured to apply force, or a significant portion thereof, in the direction of the urging of paddle 24. Surface 220 may provide additional benefits where the patient surface comprises a cushion or other soft element, e.g., where the patient may sink into the patient surface. Additionally and/or alternatively, apparatus 200 allows the patient to be transferred from a patient transportation device to a medical imaging or treatment system without removing apparatus 200. In certain situations, such as emergency situations, transferring and/or transporting a patient between two or more medical treatment or imagining systems in a timely fashion is critical to the care of the patient. Accordingly, in such situations, apparatus 200 may offer unique advantages over conventional compression devices.

Figure 11:
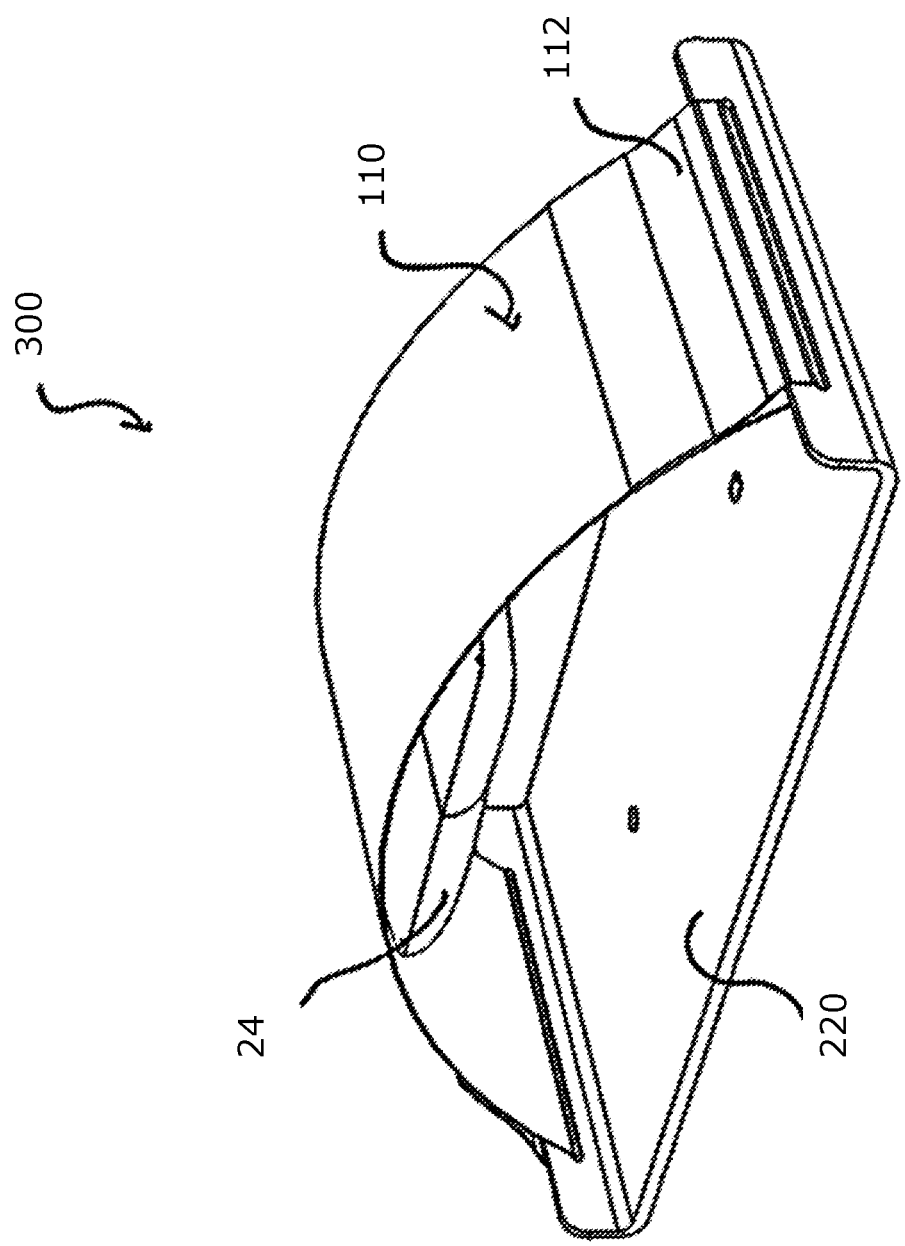
FIG. 11 is a perspective view of an apparatus for promoting shallow breathing of a patient according to a fifth embodiment of the present invention.
Figure 12:
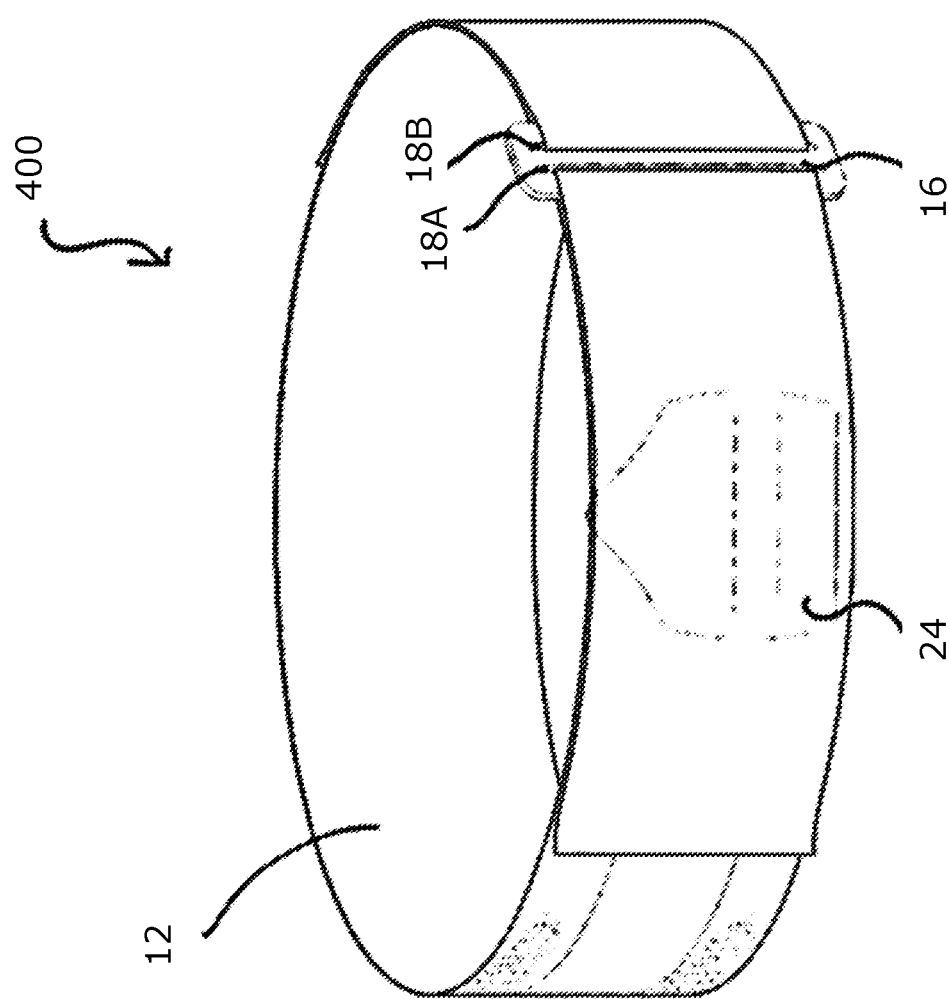
FIG. 12 is a perspective view of a paddle attached to a compression belt in accordance with a sixth embodiment of the present invention.
Figure 13:
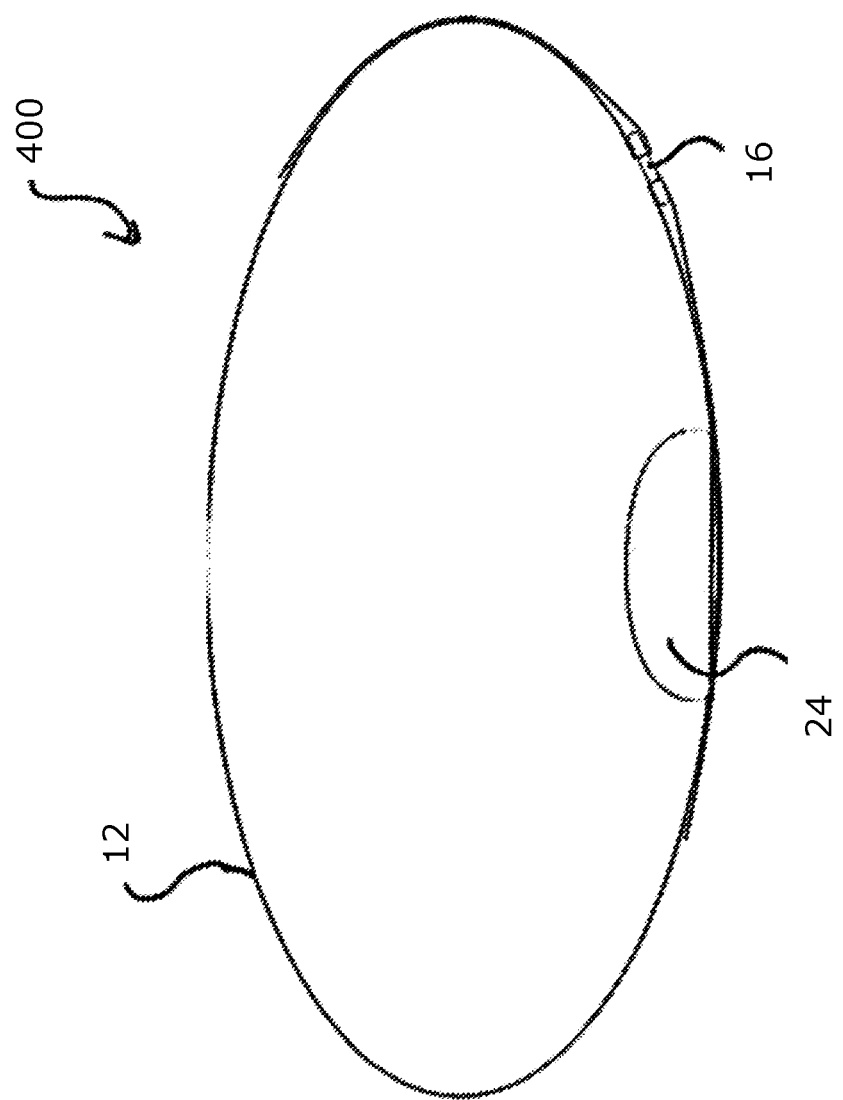
FIG. 13 is a top view of the paddle and compression belt of FIG. 12.
Figure 14:
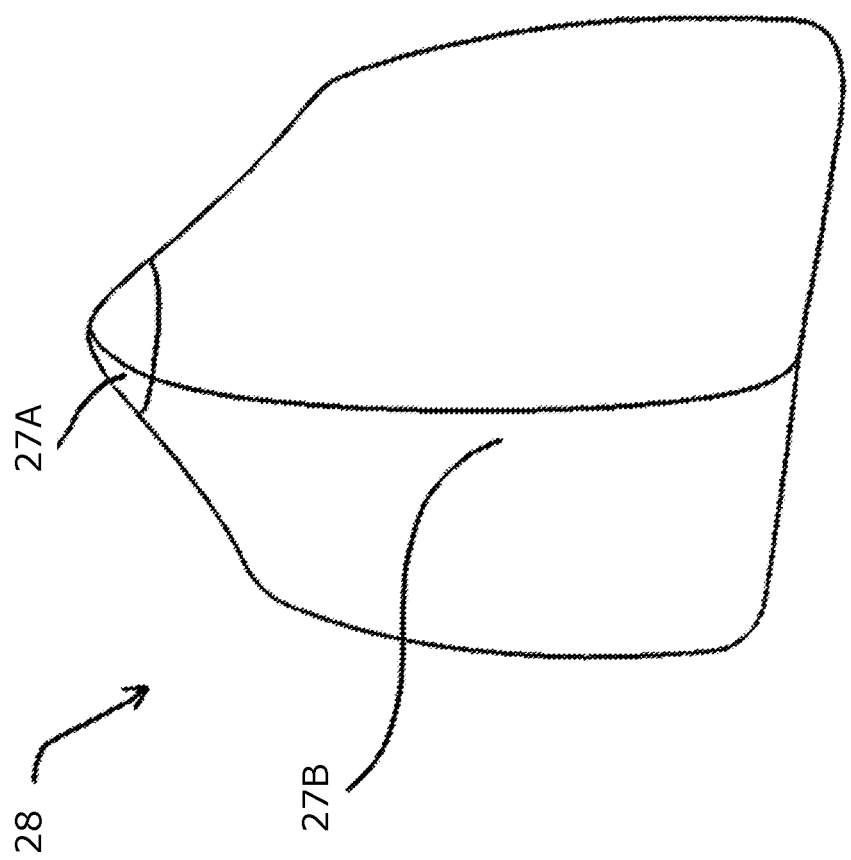
FIG. 14 is a perspective view of an embodiment of a paddle according to aspects of the present invention.

FIGS. 11-13 illustrate two embodiments (apparatus 300 and 400) of the invention that do not include a bladder. As a general overview, apparatus 300 includes paddle 24, belt 110, and surface 220. Apparatus 300 is configured to apply pressure to the patient by tightening belt 110, such that the paddle 24 is urged toward the patient and/or surface 220. As a general overview of apparatus 400, a paddle 24 and belt 12 are included. Belt 24 is configured to wrap around the patient such the end regions of the belt 12 may be folded onto itself, each other, or a different portion of belt 12, such that the end regions couple to belt 12. As shown in the embodiment illustrated in FIG. 12, at least one end region of belt 12 is inserted through a respective slot 18*a*, 18*b* of a belt loop 16 before coupling to belt 12 by way of hook and loop fasteners 14*a*, 14*b*. In a preferred embodiment, the belt includes a tightening system to urge the paddle 24 towards the patient.

It will be appreciated that various components of an apparatus for promoting shallow breathing of a patient may be separate components, integrated components, coupled components, or components configured in various combinations. More specifically, when the apparatus for promoting shallow breathing of a patient includes a paddle, a belt, and a bladder, one or more of those components can be combined or integrated. For example, as noted previously, the paddle and the bladder can be separate components or can, alternatively, be integrated into one component providing a bladder portion and a paddle portion. Also, a single component can be utilized to provide the functions of the paddle and the bladder. Additionally, the belt and paddle can be separate components or can be integrated into a single component in which the paddle is formed as an integral component of the belt. Similarly, the belt and the bladder can be separate components or can be integrated into a single or a combined component. Finally, the bladder can be eliminated from the apparatus. If the bladder is eliminated or otherwise combined into the paddle, then the apparatus is preferably configured such that the paddle can be urged toward the patient.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. An apparatus for inducing shallow breathing of a patient, the apparatus comprising:
    a paddle configured to contact a body of the patient; and
    a belt configured to secure the paddle against the body of the patient;
    a bladder interposed between the belt and the paddle in an installed condition, the bladder being inflatable to urge the paddle toward the body of the patient so as to apply pressure to the abdomen of the patient; and
    wherein the paddle has a downwardly convex lower surface configured to be positioned against a diaphragm of the patient in the installed condition; wherein the paddle defines a tip region and sloped sides, the sloped sides having a curvature corresponding to a segment of an arc having a first radius and the tip region having a curvature corresponding to a segment of an arc having a second radius, wherein the first radius is greater than the second radius, such that a compression of lower ribs of the patient is avoided when the paddle contacts the body of the patient; and wherein when the bladder is expanded, the expanded bladder urges the paddle toward the body of the patient to apply a first pressure to a first area corresponding to the diaphragm of the patient and a second pressure to a second area of the patient other than the diaphragm, the first pressure greater than the second pressure.

2. The apparatus of claim 1, wherein the paddle is contoured to fit inferior to the patient's Xiphoid process and between costal cartilage of the patient.

3. The apparatus of claim 1, further comprising a pump.

4. The apparatus of claim 3, wherein the pump is releasably connected to the bladder.

5. The apparatus of claim 3, further comprising a valve configured to prevent deflation of the bladder when the bladder is disconnected from the pump.

6. The apparatus of claim 1, further comprising a means for maintaining or releasing pressure coupled to at least one of the bladder and the paddle.

7. The apparatus of claim 6, wherein the means for maintaining or releasing pressure is further configured to prevent deflation of the bladder when disconnected from a pump.

8. The apparatus of claim 1, further comprising a pressure gauge for measuring air pressure within the bladder.

9. The apparatus of claim 1, further comprising a fastener for fastening the paddle to the bladder.

10. The apparatus of claim 1, wherein the bladder comprises an expandable volume defined by at least one sheet of material and a surface of the paddle, wherein the at least one sheet of material has a peripheral area attached to the surface of the paddle.

11. The apparatus of claim 1, wherein the bladder is removably attached to the paddle.

12. The apparatus of claim 1, wherein the paddle includes fiducial markers.

13. The apparatus of claim 1, wherein the bladder maintains two parallel walls upon inflation.

14. The apparatus of claim 1, wherein the belt is comprised of nylon, PEEK composites, urethane backed nylon, PVC, or polyester.

15. The apparatus of claim 1, wherein the belt includes markings to indicate a position of at least one end region of the belt in the installed condition.

16. The apparatus of claim 1, wherein the belt comprises a fastener attached to at least one layer of material.

17. The apparatus of claim 1, wherein the apparatus is adapted to be radiolucent.

18. The apparatus of claim 1, wherein the belt is configured to wrap around the patient.

19. The apparatus of claim 1, wherein the belt includes a coupler adapted for coupling to a patient surface.

20. The apparatus of claim 1, further comprising a surface coupled to the belt, wherein the surface and belt are configured to apply pressure to the patient.

21. The apparatus of claim 1, wherein the second area is an abdominal area adjacent the lower ribs of the patient.

22. A method of inducing shallow breathing of a patient comprising:
    positioning a paddle and a bladder relative to a belt, such that the bladder is interposed between the paddle and the belt in an installed condition;
    positioning the paddle over the abdomen of the patient;
    inflating the bladder to urge the paddle toward the body of the patient so as to apply pressure to the abdomen of the patient;
    wherein the paddle has a downwardly convex lower surface configured to be positioned against a diaphragm of the patient in the installed condition; wherein the paddle defines a tip region and sloped sides, the sloped sides having a curvature corresponding to a segment of an arc having a first radius and the tip region having a curvature corresponding to a segment of an arc having a second radius, wherein the first radius is greater than the second radius, such that a compression of lower ribs of the patient is avoided when the paddle contacts the body of the patient; and wherein when the bladder is expanded, the expanded bladder urges the paddle toward the body of the patient to apply a first pressure to a first area corresponding to the diaphragm of the patient and a second pressure to a second area of the patient other than the diaphragm, the first pressure greater than the second pressure.

23. The method of claim 22, wherein the step of positioning the paddle over the abdomen of the patient includes positioning the tip region of the paddle below the sternum and inferior to the patient's Xiphoid process and between costal cartilage of the patient.

24. The method of claim 22, wherein the second area is an abdominal area adjacent the lower ribs of the patient.

25. An apparatus for inducing shallow breathing of a patient, the apparatus comprising:
    a surface configured for contacting a body of the patient, the surface being contoured to have a tip region positioned below the sternum of the patient and to fit inferior to the patient's Xiphoid process and between a costal cartilage of the patient, the surface also being contoured to avoid compression of lower ribs of the patient when the surface contacts the body of the patient;
    a belt configured to secure the surface against the body of the patient and configured to apply pressure to the patient, thereby inducing shallow breathing of the patient; and
    a bladder interposed between the belt and the surface in an installed condition, the bladder being inflatable to urge the surface toward the body of the patient so as to apply pressure to the abdomen of the patient; and a paddle defining the surface and wherein the paddle defines the tip region and defines sloped sides, the sloped sides having a curvature corresponding to a segment of an arc having a first radius and the tip region having a curvature corresponding to a segment of an arc having a second radius, wherein the first radius is greater than the second radius, such that the compression of lower ribs of the patient is avoided when the paddle contacts the body of the patient; wherein the bladder and the paddle are separate from one another and positionable adjacent to one another; wherein the surface has a downwardly convex lower surface configured to be positioned against a diaphragm of the patient in the installed condition, and
    when the bladder is expanded, the expanded bladder urges the surface toward the body of the patient to apply a first pressure to a first area corresponding to the diaphragm of the patient and a second pressure to a second area of the patient other than the diaphragm, the first pressure greater than the second pressure.

26. The apparatus of claim 25, wherein the second area is an abdominal area adjacent the lower ribs of the patient.

* * * * *